US011554196B2

(12) United States Patent
Heschel et al.

(10) Patent No.: US 11,554,196 B2
(45) Date of Patent: Jan. 17, 2023

(54) BIOMATERIAL

(71) Applicants: Matricel GmbH, Herzogenrath (DE); Charité - Universitaetsmedizin Berlin, Berlin (DE)

(72) Inventors: Ingo Heschel, Herzogenrath (DE); Hans Leemhuis, Aachen (DE); Georg Duda, Berlin (DE); Aarón Xerach Herrera Martín, Berlin (DE); Ansgar Petersen, Berlin (DE)

(73) Assignees: MATRICEL GMBH, Herzogenrath (DE), part interest; CHARITÉ - UNIVERSITAETSMEDIZIN BERLIN, Berlin (DE), part interest ( * ) Notice: Subject to any disclaimer, the term of this patent is extended or adjusted under 35 U.S.C. 154(b) by 296 days.

(21) Appl. No.: 16/313,937

(22) PCT Filed: Jun. 28, 2017

(86) PCT No.: PCT/DE2017/000183
§ 371 (c)(1),
(2) Date: Dec. 28, 2018

(87) PCT Pub. No.: WO2018/001401
PCT Pub. Date: Jan. 4, 2018

(65) Prior Publication Data
US 2020/0179570 A1    Jun. 11, 2020

(30) Foreign Application Priority Data

Jun. 30, 2016 (DE) .................... 10 2016 007 931.2

(51) Int. Cl.
| | | |
|---|---|---|
| *A61L 27/56* | (2006.01) | |
| *A61F 2/28* | (2006.01) | |
| *A61L 27/18* | (2006.01) | |
| *A61L 27/24* | (2006.01) | |
| *A61L 27/58* | (2006.01) | |
| *A61F 2/30* | (2006.01) | |

(52) U.S. Cl.
CPC .............. *A61L 27/56* (2013.01); *A61F 2/28* (2013.01); *A61L 27/18* (2013.01); *A61L 27/24* (2013.01);
(Continued)

(58) Field of Classification Search
CPC .......... A61L 27/18; A61L 27/56; A61L 27/54; A61L 27/58; A61L 27/20; A61L 17/105; A61L 2430/34; A61L 27/52; A61L 27/26; A61L 31/06; A61L 2430/02; A61L 27/50; A61L 2430/04; A61L 27/48; A61L 31/148; A61L 2430/38; A61L 27/24; A61L 2300/416; A61L 27/16; A61L 31/146; A61L 31/16; A61L 2300/404; A61L 2400/06; A61L 2300/414; A61L 27/227; A61L 27/34; A61L 27/3604; A61L 27/38; A61L 2300/64; A61L 2430/40; A61L 24/043; A61L 27/12; A61L 27/3683; A61L 27/46; A61L 27/507; A61L 17/005; A61L 17/06; A61L 17/12; A61L 2400/18; A61L 2430/06; A61L 2430/22; A61L 27/3687; A61L 27/3834; A61L 27/3839; A61L 2300/252; A61L 2420/02; A61L 2430/10; A61L 2430/16; A61L 2430/32; A61L 27/06; A61L 27/14; A61L 27/22; A61L 27/225; A61L 27/3633; A61L 27/365; A61L 27/3804; A61L 27/3847; A61L 27/44; A61L 27/446; A61L 27/60; A61L 31/005; A61L 31/10; A61L 31/129; A61L 31/14; A61L 2300/256; A61L 2300/406; A61L 2300/43; A61L 2400/12; A61L 2400/16; A61L 2420/06; A61L 2430/14; A61L 2430/24; A61L 27/047; A61L 27/222; A61L 27/36; A61L 27/3608; A61L 27/362; A61L 27/3637; A61L 27/3691; A61L 27/3821; A61L 27/3882; A61L 27/3886; A61L 27/3895; A61L 27/40; A61L 31/022; A61L 31/047; A61L 31/141; A61L 15/32; A61L 15/325; A61L 2300/114; A61L 2300/258; A61L 2300/40; A61L 2300/402; A61L 2300/412;
(Continued)

(56) References Cited

U.S. PATENT DOCUMENTS

| | | | |
|---|---|---|---|
| 6,447,701 B1 | 9/2002 | Heschel et al. | |
| 7,758,882 B2 * | 7/2010 | Roeder | ............... A61L 24/0084 424/426 |
| 8,518,123 B2 * | 8/2013 | Jensen | ................... A61L 27/44 623/23.76 |

FOREIGN PATENT DOCUMENTS

| | | |
|---|---|---|
| EP | 0 493 698 A1 | 7/1992 |
| EP | 2 450 066 A1 | 5/2012 |

(Continued)

OTHER PUBLICATIONS

Reilly et al., Intrinsic extracellular matrix properties regulate stem cell differentiation, Journal of Biomechanics 43 (2010) pp. 55-62.
(Continued)

*Primary Examiner* — Audrea B Coniglio
(74) *Attorney, Agent, or Firm* — Collard & Roe, P.C.

(57) ABSTRACT

A biomaterial, particularly for tissue regeneration, includes an open, porous bioresorbable first material portion and a second material portion that is stiffer than the first material portion, wherein the volume fraction of the stiffer material is less than 30% of the total volume of the biomaterial, and the structural stiffness of the second material portion is at least 10 times greater than that of the first material portion.

19 Claims, 4 Drawing Sheets

(52) U.S. Cl.
CPC ..... *A61L 27/58* (2013.01); *A61F 2002/30014* (2013.01); *A61F 2002/30143* (2013.01); *A61L 2430/02* (2013.01); *A61L 2430/24* (2013.01); *A61L 2430/38* (2013.01)

(58) Field of Classification Search
CPC ........... A61L 2300/602; A61L 2300/62; A61L 2300/622; A61L 2300/626; A61L 2430/00; A61L 2430/12; A61L 2430/20; A61L 24/08; A61L 24/104; A61L 26/00; A61L 27/02; A61L 27/025; A61L 27/28; A61L 27/32; A61L 27/3616; A61L 27/3625; A61L 27/3629; A61L 27/3641; A61L 27/3645; A61L 27/3662; A61L 27/3695; A61L 27/3808; A61L 27/3826; A61L 27/383; A61L 27/3873; A61L 27/3891; A61L 27/502; A61L 31/028; A61L 31/044; A61L 31/127; A61L 31/128; A61L 31/145; A61L 33/18; A61K 2300/00; A61K 6/30; A61K 6/887; A61K 31/551; A61K 31/13; A61K 31/201; A61K 31/352; A61K 31/365; A61K 31/4045; A61K 31/513; A61K 31/522; A61K 31/7056; A61K 31/706; A61K 31/7064; A61K 31/7072; A61K 31/727; A61K 31/765; A61K 35/12; A61K 35/35; A61K 35/36; A61K 35/44; A61K 38/00; A61K 38/18; A61K 45/06; A61K 8/64; A61K 9/0024; A61K 9/5031; A61K 9/70; A61K 2800/412; A61K 2800/56; A61K 33/06; A61K 33/16; A61K 33/44; A61K 38/05; A61K 38/07; A61K 38/08; A61K 38/10; A61K 38/12; A61K 38/39; A61K 47/02; A61K 49/006; A61K 6/20; A61K 6/69; A61K 6/71; A61K 8/11; A61K 8/19; A61K 8/21; A61K 8/24; A61K 8/87; A61K 9/0051; A61K 9/0056; A61K 9/127; A61K 9/5089; A61K 2039/55522; A61K 2039/55561; A61K 2039/64; A61K 31/192; A61K 31/44; A61K 31/722; A61K 33/00; A61K 35/28; A61K 35/48; A61K 38/164; A61K 38/1875; A61K 39/0011; A61K 41/00; A61K 41/0028; A61K 47/06; A61K 47/12; A61K 47/183; A61K 47/36; A61K 47/42; A61K 47/50; A61K 47/58; A61K 47/6435; A61K 6/17; A61K 6/75; A61K 6/77; A61K 6/84; A61K 9/0019; A61K 9/0048; A61K 9/0053; A61K 9/0073; A61K 9/16; A61K 9/1647; A61K 9/5052; A61K 9/7007; A61K 9/703; A61K 9/7084

See application file for complete search history.

(56) References Cited

FOREIGN PATENT DOCUMENTS

| WO | 2009/049650 A2 | 4/2009 | |
|---|---|---|---|
| WO | WO2009/049650 A2 * | 4/2009 | ............ A51L 27/56 |

OTHER PUBLICATIONS

Cezar et al., Biologic-free mechanically induced muscle regeneration, PNAS, Feb. 9, 2016, vol. 113, No. 6, pp. 1534-1539.
Harley et al., Microarchitecture of Three-Dimensional Scaffolds Influences Cell Migration Behavior via Junction Interactions, Biophysical Journal, vol. 95, Oct. 2008, pp. 4013-4024.
Tse et al., Stiffness Gradients Mimicking In Vivo Tissue Variation Regulate Mesenchymal Stem Cell Fate, PLoS ONE, vol. 6, Issue 1, Jan. 2011, pp. 1-9.
Engler et al., Matrix Elasticity Directs Stem Cell Lineage Specification, Cell 126, Aug. 25, 2006, pp. 677-689.
Park et al., The effect of matrix stiffness on the differentiation of mesenchymal stem cells in response to TGF-$\beta$, Biomaterials 32, Elsevier, 2011, pp. 3921-3930.
International Search Report of PCT/DE2017/000183, dated Oct. 19, 2017.
Weisgerber D W et al., "Evaluation of multi-scale mineralized collagen-polycaprolactone composites for bone tissue engineering", Journal of the Mechanical Behavior of Biomedical Materials, vol. 61, Apr. 6, 2016, pp. 318-327.

* cited by examiner

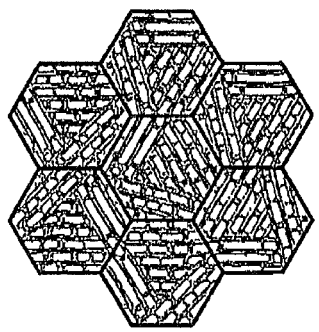
Fig. 7
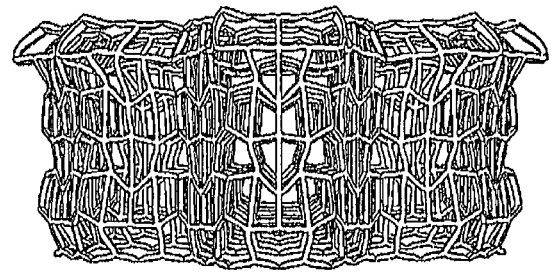
Fig. 8
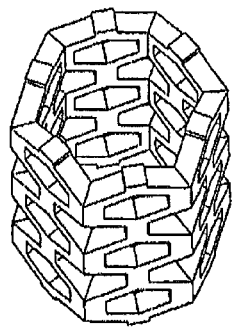 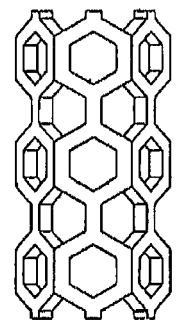
Fig. 9
| Porosity of the two material components [%] | Minimum values of the relative structural stiffness of the two material components [%] (relative structural stiffness = structural stiffness / material stiffness) |
|---|---|
| 47 | 33.5 |
| 58 | 21.7 |
| 82 | 3.9 |
| 88 | 1.6 |
| 93 | 0.6 |
| 97 | 0.1 |
Fig. 10

BIOMATERIAL

CROSS REFERENCE TO RELATED APPLICATIONS

This application is the National Stage of PCT/DE2017/000183 filed on Jun. 28, 2017, which claims priority under 35 U.S.C. § 119 of German Application No. 10 2016 007 931.2 filed on Jun. 30, 2016, the disclosure of which is incorporated by reference. The international application under PCT article 21(2) was not published in English.

BACKGROUND OF THE INVENTION

1. Field of the Invention

The invention relates to a biomaterial. This is a synthetic or non-living natural material which is used in medicine for therapeutic or diagnostic purposes, and in this case in direct contact with biological tissue of the body.

The material enters into chemical, physical and biological interactions with the corresponding biological systems.

This also includes short-term contact over the outer body surface, via body openings and via externally accessible mucous membranes. The invention relates in particular to those materials which are introduced inside the body for longer-term retention.

In this case, the term biomaterial refers to the properties of the material, in particular the chemical and physical properties. Characteristic of a biomaterial is a biocompatibility resulting from its properties, which includes both the functional similarity to the body's own structures and reasonable biological compatibility in the body.

2. Description of the Related Art

Many biomaterials are used in the form of implants inside the body. In this case, they serve, for example, in the context of a treatment to support healing after a bone fracture designated as osteosynthesis, as well as the permanent replacement of bones that were irreparably destroyed by an accident or bone cancer. Also possible is the replacement of joint structures that are worn out due to chronic illness or long-term stress. Blood vessels can be replaced with vascular prostheses, stents serve to support the wall of blood vessels. Examples of replacement of organ parts or whole organs by biomaterials are artificial heart valves, artificial urinary bladders or artificial hearts. Biomaterials are also used in plastic surgery, such as glass for artificial eyes, silicone for breast reconstruction or enlargement or titanium for skull reconstruction.

However, biomaterials also serve to support tissue regeneration, in which the damaged or missing tissue is reshaped and/or rebuilt by the body so that it is equivalent in function to the original intact tissue or at least close to it. In this case, the biomaterial has no permanent but rather only a temporary function and is ideally degraded in the body over time until it completely disappears and is replaced by the newly formed tissue. Examples include the regeneration of bones, skin, nerves, muscles, tendons and ligaments, connective tissue, cartilage, esophagus, vocal cord, heart muscle, heart valves. The biomaterials used for this purpose must therefore have further properties, since they in particular must be degraded or remodeled at least in part by processes taking place in the body, wherein the degradation products must also be biocompatible. Such "bioresorbable" biomaterials can consist of natural materials of autogenous, allogeneic or xenogeneic or plant origin (such as collagen, elastin, fibrin, hydroxyapatite, chitosan, alginate) or synthetic materials (such as PLA, PGA, PCL, PLGA).

The complete restoration of the function of damaged, diseased or lost tissue (for example, through trauma) is sought in regenerative medicine. Regenerative medicine is concerned both with so-called "tissue engineering", the growth of replacement tissue having properties which are identical or as similar as possible to the tissue to be replaced, but also with the restoration of the function by utilizing the body's own so-called "endogenous" regeneration mechanisms and principles. Endogenous regeneration mechanisms can be supported, for example, by the introduction of biomaterials, cytokines (for example, growth factors) or cells or a combination thereof. Insofar as the biomaterial, for example, by its mechanical, physical or chemical properties, is capable of recruiting cells from the surrounding tissue and of supporting and guiding it in the endogenous regeneration process, a pure biomaterial approach is also conceivable, in which cells or cytokines do not need to be introduced into the body from the outside.

The principle of using endogenous regeneration processes for tissue regeneration has led to contradictory results regarding the quality of the resulting tissue using existing biomaterial approaches. The lack of quality of the regeneration and an associated unclear long-term success lead to the fact that until now few or none of these ready-made and ready-to-use "off the shelf" materials or material combinations could win recognition for tissue regeneration in the clinic.

In so-called tissue-engineering approaches, the most accurate replication of the intact tissue should ensure rapid integration of the biomaterial and restoration of the tissue function. However, the complexity of the native tissue has not been completely reproducible so far, so that corresponding tissue engineering products are not so far comparable to native autologous tissue.

SUMMARY OF THE INVENTION

The object of the invention is to find a material that makes it easier for a structural and/or functional change within the organism to restore the original situation or to achieve a desired situation.

This object is achieved with a biomaterial having the features according to one aspect of the invention and a method having the features according to another aspect of the invention.

Advantageous embodiments are discussed below.

The subject matters of the embodiments are also independently essential. The disclosure thus also extends to invention subjects in which the volume fraction of the stiffer material is not less than 30% of the total volume of the biomaterial.

In order to be able to determine the material fraction, when material qualities merge into each other as a fluid transition or when the stiffness of a similar material is substantially determined by the structure, it is determined that the first material fraction is that fraction which has a lower stiffness than the average stiffness of the biomaterial. The average stiffness is determined based on the volume.

The volume fraction of the stiffer material is understood to mean the actual volume of the second material fraction excluding the cavities in relation to the total volume of the biomaterial. The total volume is in each case the volume of the mass plus the volume of the cavities enclosed by the mass. That is, a porous cuboid has the same total volume as an equally large solid material.

Studies, for example, by Engler et. al., Harley et. al., Park et al. and Reilly et. al. have shown that stem cell migration and differentiation are critically influenced by the characteristics of stiffness and structure of the microenvironment of the cell.

Further studies in 3D hydrogels confirmed that a mechanical stiffness having an elastic modulus between approximately 10 and 100 kPa induces osteogenic differentiation of mesenchymal stem cells (MSCs), while lower stiffnesses leads to adipogenic differentiation.

Experimental studies and computer models have shown that in addition to the substrate stiffness, local mechanical elongation or compression also represents a decisive influencing factor for the differentiation of cells and tissues during bone regeneration. In the following, the term "compression" should also be subsumed under the generic term "elongation", so that the numbered elongations should also include shortenings by the amount percentage. Excessively high elongations ($\varepsilon > 30\%$) impede regeneration, medium elongations ($\varepsilon =$approx. 4 to 12%) support the formation of cartilage, small elongations ($\varepsilon =$approx. 0.04 to 4%) support the mineralization of cartilage and the formation of bones.

In the invention, the mechanics of the material, on the one hand, should be used to stabilize the softer material fraction during the regeneration process and, on the other hand, to be used as a regulator of cell functions and tissue differentiation. The forces acting on the material are translated into the necessary elongation for the respective differentiation via the spatially specific design of the components. The material should also experience a spanning function through the structure which should prevent collapse of the softer biomaterial structure during the healing process.

One embodiment provides for a multi-component biomaterial which consists of at least two components that differ primarily in their mechanical and structural properties. The biomaterial referred to hereinafter as "mechano-hybrid scaffold" is hierarchically constructed mechanically and structurally. In the two-component biomaterial, the component having lower stiffness and lower structure size (first material fraction) serves as a support material for the cells that are to effect regeneration (of local origin or obtained and/or cultured) and as cell-controlling material; the component having higher structural stiffness and structure size (second material fraction) serves as a mechanically stabilizing element for realizing the desired macroscopic properties. Stiffness here means structural stiffness. This is determined by the properties of the materials used, their structure and by the geometric arrangement of the components in multi-component materials. The first material fraction is structurally integrated into the second material fraction in a form-locking manner. Mechanical forces that act on the second material fraction are thus transferred to the first material fraction preferably both via a form fit and adhesion forces between the two material components via adhesion, wherein the stiffness at a corresponding mechanical load determines the elongation acting by the second material fraction in the first material fraction. In this case, the term "scaffold" refers to "scaffold structures" which can be partially or completely remodeled during the course of regeneration by the body's own processes.

The function of structuring the mechano-hybrid scaffold is primarily to direct the regeneration process along a predetermined direction. This principle has already been successful in the regeneration of, for example, skin, soft tissue and peripheral nerves (U.S. Pat. No. 6,447,701 (B1)—Method for producing porous structures) and used by the inventors in the regeneration of bone. As expected, however, a structured and directed regeneration process is also important for the regeneration of many other tissues (for example, muscle, tendons, ligaments, vessels, tubular hollow organs). Accordingly, at least one of the material fractions usually has a structural anisotropy. The structurally hierarchical structure also ensures in this case that the architecture and the local mechanical stiffness of the first material fraction are influenced as little as possible by the second.

In specific animal studies, it was proven that even the first material fraction alone with a suitable choice of material parameters (stiffness, pore architecture, absorbability) can support the bone regeneration process in a bone defect. In the studies, bone growth along the scaffold pores was observed via the process of endochondral ossification, whereas in the same animal model without scaffold, a direct (so-called intramembranous) shallow bone formation and lower volumetric bone formation were observed. In endochondral ossification, bone is formed via the mineralization of a cartilage phase, as observed in the growth plate in children and adolescents. In contrast, in direct intramembranous bone formation, bone tissue is deposited directly on existing bone without cartilage phase. However, it has also been observed that in this approach, the soft first material fraction mechanically and structurally optimized for induction in the body is deformed by cell forces and forces from surrounding tissue, and its pore architecture is compromised and loses its guiding function. It is therefore necessary to combine the first material fraction with a second mechanically stabilizing material fraction in order to maintain upright or further increase the regeneration potential of the material. In addition, with a second mechanically stabilizing material fraction, the stiffness of the first material fraction can be further reduced, so that even larger elongations by the cells that is more advantageous for the tissue regeneration of certain tissue can be achieved by the cells without the overall structure of mechano-hybrid scaffold collapsing.

It is advantageous when at least one material fraction and preferably both material fractions have directional structures. A structure is directed when the largest and the smallest distance between structural elements (pore walls, webs, etc.) that are to be found along all spatial directions differs at least threefold. The direction having the greatest distance of the structural elements corresponds to the preferred orientation of the material or the direction of the structural anisotropy.

In one possible realization, one or both material fractions are biodegradable. In this case, resorbability is matched to the speed of the regeneration process and the ongoing tissue remodeling processes. Both material fractions are connected to each other in so far as form or force fit so that mechanical signals are transmitted from one to the other material fraction.

The anisotropic structuring of the first and/or second material fraction additionally allows the realization of different mechanical stiffnesses in different spatial directions (anisotropic stiffness). This makes it possible to design the mechano-hybrid scaffold so that it is easily compressible, for example, perpendicular to the load-bearing direction, which offers great advantages with introduction by means of minimally invasive surgical methods (for example, endoscopy). Elastic material properties ensure the respanning of both material fractions after minimally invasive insertion.

It is therefore proposed that at least one material fraction and preferably even both material fractions are elastically deformable. The range of elastic deformability in a spatial direction is in practice at a compression to a minimum of 0.1 times the length or in the case of elongation, to a maximum of 10 times the length.

The first material fraction can consist of a plurality of materials or components, which are arranged, for example, in the form of a bi- or multi-layer scaffold. These can differ in the material (for example, hydrogel, collagen, chitosan, etc.) or in the material parameters (for example, solids content, density, porosity, etc.). Likewise, the second material fraction can consist of a plurality of materials or components and be constructed as a bi- or multi-layer scaffold. The mechanical properties of the material fractions can be designed spatially different, either as discrete layers or with flowing (gradual) transition or with a soft or solid core. Such a design can be used, for example, to realize different elongations in different regions of the material. As a result, for example, transitions between different tissues can be modeled (for example, muscle tendon, tendon bone, cartilage bone). The spatial differences in, for example, elongation, pore size or stiffness can be used to differentiate the regenerating tissue into different tissue types within a material.

It is advantageous when a first and a second material fraction are structurally interwoven with each other and not designed as discrete layers. The support structure can not only be designed as a sheath around the soft scaffold, but also, like an endoskeleton, be integral and part of the biomaterial surrounded by the scaffold. (Def from Wikipedia: In biology, an endoskeleton (also called internal skeleton) is regarded as a mechanical support structure (skeleton), which is not part of the outer shell of the organism.) However, the support structure can possibly also be part of the shell and then the term endoskeleton does not apply exactly.

The hierarchically-structured biomaterial can additionally include other components in the form of growth factors, bioactive particles or additives that modify the bioactivity of the material. The additional factors can be integrated into the first material fraction and/or the second material fraction or introduced into the porous structure.

The hierarchically structured biomaterial can additionally be combined, prior to introduction into the body, with cells which support the regeneration process. These cells can either be obtained during the procedure (for example, from tissue or blood) or removed in a previous procedure and, if necessary, have been preserved and/or expanded in vitro.

The invention has several advantages over known scaffolds. The guide structure requires a structural and/or mechanical anisotropy of at least one of the fractions for aligning the tissue regeneration process in tissues having specific structural properties, such as bones, ligaments, muscles and/or cartilage. Bimodal mechanical properties require a microscopically soft and macroscopically load-bearing function at the cellular level to stabilize scaffold integrity.

A hierarchical structure enables optimized mechanics and geometry on different length scales with the same construction principle, which leads to special mechanical and geometric properties, and also enables the seamless transmission of mechanical signals between the components. The structure of different material fractions enables spatially adjustable mechanical properties. A spanning-function of the support structure achieves a mechanical long-term stability, that is, a dimensional stability of biodegradable scaffolds. If at least the second material fraction has a compressibility and elasticity, a scaffold results, which is particularly suitable for use in minimally invasive surgical techniques. In this case, a mechanical anisotropy (very fixed in mechanical functional direction, easily compressible perpendicular thereto) can be used. The second material fraction spans the first material fraction after compression. Individual components or material fractions can be optimized mechanically, structurally and possibly biochemically for the respective task. In this case, the first material fraction can be optimized for the control of cellular processes and the second material fraction for stabilizing the primary structure and for transmitting biomechanical signals to the first material fraction. This allows a discrete distribution or a continuous transition of the mechanical properties of the material. A complete integration of the components into each other is also possible. Mechanical, chemical, biological and physical properties can be enhanced by combining or integrating particles or additives/agents. In addition, the possibility of tent settlement is opened up.

The following materials can be used as examples for the realization of both components: In principle, all soft and degradable, biocompatible materials, individually or in combination, are suitable for the first material fraction. These are, for example, collagen, fibrin, hyaluronic acid, elastin, alginate, polyethylene glycol (PEG), polyvinyl alcohol (PVA), polysaccharides, chitosan, silk and other materials. In principle, all degradable and non-degradable biocompatible materials are suitable for the second material fraction. These are, for example, polyamide (PA), polycaprolactone (PCL), polylactide-co-glycolide (PLGA), polylactide (PLA), polyethylene glycol (PEG), polyglycolide (PGA), polyvinyl alcohol (PVA), polyetheretherketone (PEEK), polymethylmethacrylate (PMIVIA), metals (for example, nitinol, surgical steels, titanium and titanium alloys, magnesium), ceramics and ceramic composites and many other materials.

Various material parameters can be used as an example for the realization of the two components. With regard to the structure, a highly porous structure having a porosity>70% and an open-porous spherical, channel-shaped or more complex geometry is proposed for the first material fraction. For the second material fraction, a framework structure having the lowest possible material volume or high porosity (>70%) is proposed, which is constructed, for example, from polygonal elements (honeycomb structure), channels or spherical geometries. The pores or structure sizes can be between 10-1000 μm for the first material fraction and between 100 μm-10 mm for the second material fraction. The stiffnesses can be E<1 MPa for the first material fraction and E>100 kPa for the second material fraction. For the first material fraction, a material is proposed which, after cyclic compression and decompression, does not substantially change its shape (pore geometry) in combination with the second material fraction and for the second material fraction an elastic, largely reversibly deformable material having little or no energy dissipation in a cyclic compression and decompression.

It is generally known that the porosity of a biomaterial for the utilization of endogenous regeneration processes for tissue repair should be as high as possible. A high porosity enables a better supply of the cells by means of diffusion and convection of dissolved substances (for example, supply of nutrients and oxygen, removal of metabolic products and gases). In addition, a high porosity is necessary to spatially not interfere with the endogenous tissue processes by the biomaterial. On the other hand, since the external mechanical stiffness of the biomaterial described in the invention is essential to the functionality of the first material fraction, the architecture of the second material fraction is selected so that its structural stiffness is as high as possible in comparison to the volume fraction it occupies. This is only possible through a corresponding design process that takes engineering principles into account. Our own computer simulations using the finite element method (FEM) have shown that such a process can significantly increase the structural stiffness of the second material fraction relative to the stiffness of the material used. Only then, taking into account the necessary stiffness of the biomaterial, for example, for use in bone defects, porosities of >70 percent by volume (70% (v/v), can this be achieved. The stiffness specified in FIG. 13 can be achieved or exceeded (structure according to the embodiment in FIG. 6) through the design of the second material component. Intermediate values are to be calculated by interpolation. Stiffness is structural stiffness in MPa and porosity is porosity in percent by volume. The prior art (Weisgerber et al., 2016) shows only a relative structural stiffness of 6.3% at a porosity of 67 percent by volume, the value of a design-optimized structure is >15%. The relative structural stiffness is the structural stiffness divided by the material stiffness).

In a publication, Weisgerber et al. (Journal of the Mechanical Behavior of Biomedical Materials 2016, Volume 61, Pages 318-327, DOI: 10.1016/j.jmbbm.2016.03.032) showed that the stiffness of a soft biomaterial (mineralized collagen/glycosaminoglycan scaffold) can be significantly increased by combining it with a printed stabilizing structure (polycaprolactone, PCL). However, the porosity of the stabilizing structure is low (67 percent by volume), so that a significant impairment of endogenous regeneration processes during implantation is to be expected. In addition, both material components have no directed structures and thus can not direct the regeneration process along defined directions, which is disadvantageous for the regeneration of musculoskeletal tissue and other tissues having directed structures (for example, nerves). The aim of the invention is to provide a structurally and mechanically optimized environment for tissue regeneration. For this purpose, porosities with values >70 percent by volume, more preferably >80 percent volume, are necessary. For resorbable materials, such porosities can be achieved while maintaining the mechanical structural stiffness only by a material architecture matched to the mechanical function. Here, the amount of material is distributed so that in the desired spatial direction results in the highest possible structural stiffness. The identification of an optimal architecture is possible, for example, using "finite element" computer simulations.

Furthermore, the stabilization structure proposed by Weisgerber within the unit cell has very different material thicknesses/material diameters. This results in an inhomogeneous absorption in the course of material degradation after implantation. Regions of small diameter material are degraded faster and lead to mechanical failure of the structure. In the course of degradation over a longer period of time, regions of large material diameter lead to a tissue reaction without fulfilling a mechanical function. For this reason, the most uniform possible diameter of the structural elements within a unit cell is advantageous.

It is particularly advantageous when the first material fraction consists of collagen and is optimized in terms of solids content, pore size and degradation time. Such an embodiment could induce bone growth via a cartilage phase (endochondral ossification) in a bone defect of critical size.

The material can be used in different regions of tissue defect regeneration. A particularly relevant application lies in vertebral body fusion, the regeneration of larger defects of the long bones and in the regeneration of osteochondral defects, for example, in the knee joint. In addition to these applications, the use of the material in the regeneration of tendons, tendon-muscle and tendon-bone transitions after rupture should be mentioned. For this purpose, for example, bone regeneration materials for the healing of bone defects, for example, in tibia or radius, bone regeneration material for fusion of vertebral bodies, material for the regeneration of osteochondral defects, for example, after trauma or osteochondritis dissecans, material for the regeneration of hollow-organs (vessels, esophagus, etc. . . . ), material for the regeneration of vocal cords, material for the regeneration of skin, material for the regeneration of heart valves and heart muscle and material for the regeneration of peripheral nerves and the central nervous system (spinal cord) are produced from the biomaterial.

The structure of both material components can be constructed from simple basic geometries/basic structures. Such a basic structure can, analogously to crystallography, be described as a unit cell, from which the overall structure is created by displacement and/or rotation in certain spatial directions or along specific axes. This creates a repetitive pattern having structural symmetries in displacement and rotation.

It is particularly advantageous when the second material fraction has stiffening structures. The volume or the mass of the second material fraction can be distributed so that the highest possible mechanical stiffness or strength (or even extensibility) results in the lowest possible volume of material or at the highest possible porosity. This can be achieved, for example, by a suitable arrangement of thin material webs or walls in certain spatial directions (=lightweight construction). These structures can be constructed, for example, like honeycombs.

It is particularly advantageous when the component of at least one material fraction and preferably both material fractions contains substances, elements or structures which can be displayed by means of imaging methods used in the clinic, so that the alignment and positioning of the biomaterial can be checked with the help of X-ray images, images in computer tomography or by magnetic resonance imaging and the healing process can be controlled.

It is particularly advantageous when the first or second material fraction can be changed in shape by an external stimulus (for example, force, temperature, electric or magnetic fields), for example, to induce cyclic deformations, which have mechanobiological effects on the regenerating cells. The triggered deformation of the second material fraction can facilitate minimally invasive implantation of the biomaterial. Ideally, the external stimulation is performed non-invasively, that is, it works (for example, by the magnetic field) without touching the biomaterial. Cyclic deformation of the biomaterial can be advantageous for the targeted differentiation of the cells and the nature and orientation of the extracellular matrix formed by the cells.

Biologic-free bone-induced muscle regeneration, Proc Natl Acad Sci USA. 2016 Feb. 9; 113(6):1534-9. doi: 10.1073/pnas describes the mechanical deformation of a ferrogel having magnetic particles by applying a magnetic field. In contrast to the invention, it is a one-phase material without alignment and without support structure. For the explanation of the invention, however, reference is made in full to this publication.

In a method for producing such a biomaterial, the second material fraction of an implant for regeneration of a specific tissue is adjusted such that the elongations required for the regeneration of this tissue result in the first material fraction in the body and collapse of the first material fraction is prevented.

First, for this, the stiffness of the intact material and the mechanical forces acting there are taken from the literature. Furthermore, values of tissue elongation, which are particularly conducive to a regeneration process, are taken from the literature. With the help of a 3D design software (CAD), unit cells are designed which adapt the stiffness in the different spatial directions to the forces occurring after implantation (for example, greatest stiffness in the main load direction). The maximum stiffness of the material must thereby be equal to or below the stiffness of the intact tissue in order not to block a mechanical stimulus for regeneration. In the course of the process, different designs of the unit cell are tested for their mechanical properties by displacing/rotating/adding/removing individual material webs by means of computer simulations based on the finite element method. Hereby, the elongations occurring in the material are determined as a function of the acting forces. The design is selected which meets the criteria for stiffness/elongation in the different spatial directions and at the same time has the highest possible realizable porosity.

BRIEF DESCRIPTION OF THE DRAWINGS

Several embodiments are shown in the drawing and are explained in more detail below. Shown are FIG. 1 a three-dimensional view of an openly porous, bioresorbable first material fraction, FIG. 2 a three-dimensional view of a second material fraction, which is stiffer than the first material fraction, FIG. 3 a three-dimensional view of a combination of first and second material fraction, FIG. 4 a three-dimensional view of a combination of first and second material fraction having different structures, FIG. 5 a view of the integration of the combination shown in FIG. 3 into a tissue region, FIG. 6 a three-dimensional view of a mechano-hybrid scaffold, FIG. 7 a section through the mechano-hybrid scaffold shown in FIG. 6, FIG. 8 a side view of the compressed mechano-hybrid scaffold shown in FIG. 6, FIG. 9 two views of a structural element of the second material component as a basis for computer simulations, FIG. 10 the lower limit values of the relative structural stiffness of the structural element shown in FIG. 9 as a table, FIG. 11 a pure collagen scaffold (a, 1) and a mechano-hybrid scaffold (a, 2) after cutting the prototypes for mechanical testing and a support structure produced by means of SLM before introduction into the mechano-hybrid scaffold (b), FIG. 12 images of the pure collagen scaffold (a) and of the mechano-hybrid scaffold (b) after wetting with aqueous buffer solution and the result of the mechanical compression test (c) and FIG. 13 the structural stiffness over the porosity.

DETAILED DESCRIPTION OF THE PREFERRED EMBODIMENTS

Figure 1:
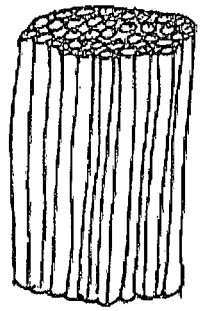

The first material fraction shown in FIG. 1 has a directed pore structure. This serves as a guide structure and at the same time represents the actual cell substrate having optimized mechanical and structural properties (for example, pore diameter) and thus the material component for induction of the regeneration processes. The mechanical properties are optimized for the cellular processes of migration, matrix formation and differentiation (intrinsic biomechanical and structural signals).

Figure 2:
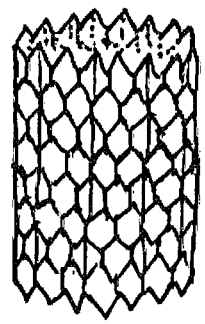

The second material fraction shown in FIG. 2 (secondary structure), in the illustrated embodiment, is also the structurally anisotropic, load-bearing support structure. It has no direct influence on the cellular processes. However, the higher stiffness of this component ensures the macroscopic integrity of the first material fraction. The stable structure realizes a spanning function and prevents the collapse of the first material fraction serving as an inner guide structure during the tissue formation and remodeling processes. In addition, the mechanical elongations that arise due to the locally acting musculoskeletal forces in the first material fraction are adjusted via the stiffness of the second material fraction. Elongation values are set which support the differentiation into the desired tissue types (for example, cartilage or bone).

Figure 3:
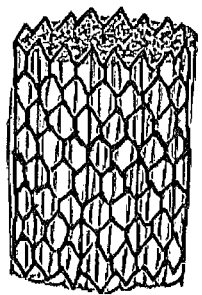
Figure 4:
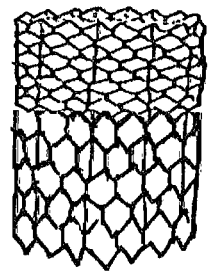

The mechano-hybrid scaffold shown in FIG. 3 represents a three-dimensional combination of first and second material fraction and FIG. 4 represents an embodiment in which the different requirements for new tissue formation (cartilage to bone) are realized by two regions of different properties. Here, the extensibility according to the cellular requirements in the lower region of the scaffold for the bony regeneration is smaller than in the upper region for the cartilage regeneration.

Figure 5:
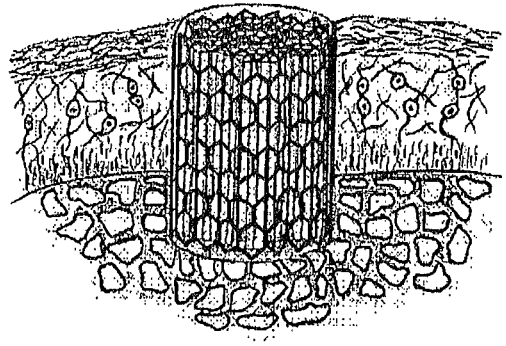

FIG. 5 shows a view for the integration of the combination shown in FIG. 3 into a tissue region of a bone cartilage defect, wherein the use of the embodiment according to FIG. 4 is an even more advantageous variant for the regeneration of the two tissue types bone or cartilage.

Figure 6:
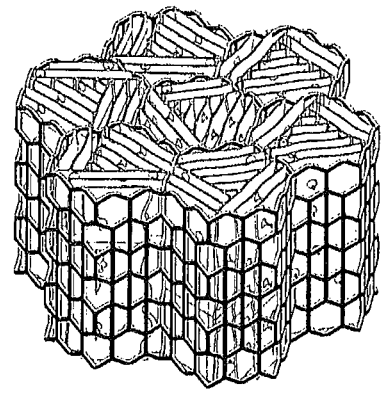

The mechano-hybrid scaffold shown in FIGS. 6 to 8 consists of a material fraction, for example, of collagen and a second material fraction, for example, of PCL. The structure of the second material fraction was optimized in terms of mechanical and structural properties (anisotropy, defined stiffness, high porosity, no struts oriented perpendicular to the longitudinal direction/pore direction). The hierarchical structure was created by duplication of unit cells from the first and second material components. The deformation from load shown in FIG. 8 was simulated by means of the finite element method for the design process to achieve the desired beneficial elongations.

Figure 11:
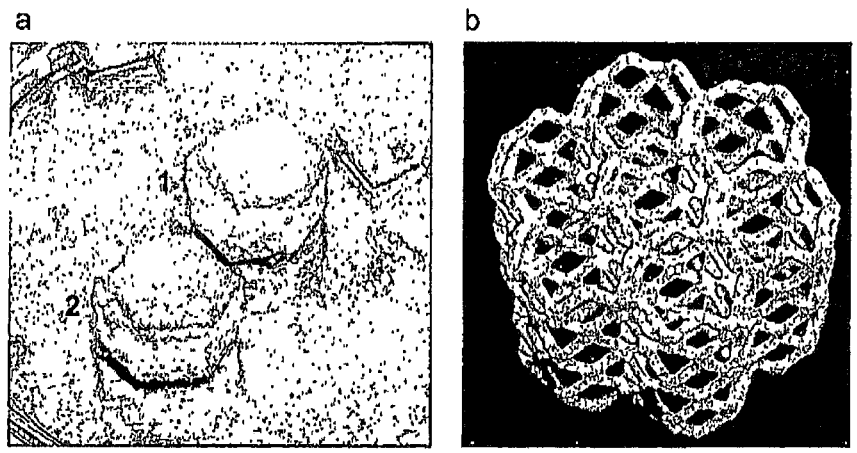

In one embodiment, a soft collagen scaffold, as a first material fraction, having vertically directed pores was combined with a 3D printed support structure as the second material fraction. The support structure was made of polyamide (PA) by means of SLM (selective laser melting). The diameter of the pores in the support structure (that is, the diameter of a honeycomb of the second material fraction) was approximately 50× greater than the diameter of the pores in the first material fraction, the collagen scaffold. The mechano-hybrid scaffold (FIG. 11 a, Scaffold 2) has been prepared by producing a very soft collagen scaffold having directed pores within the support structure (FIG. 11 b).

Figure 12:
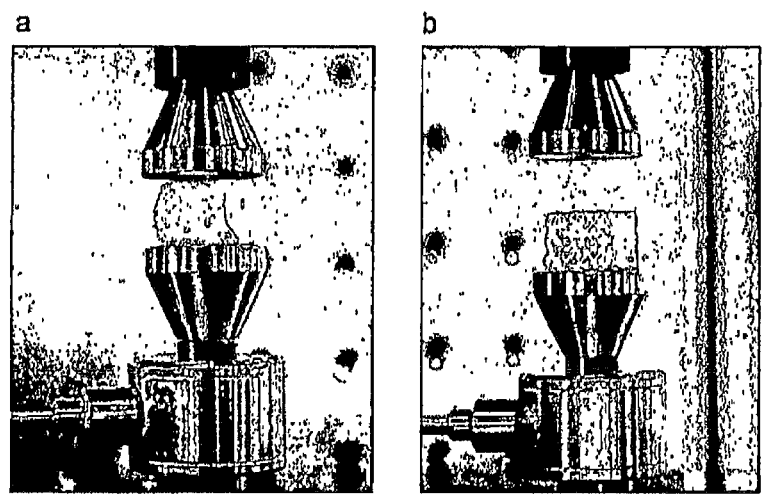
Figure 12:
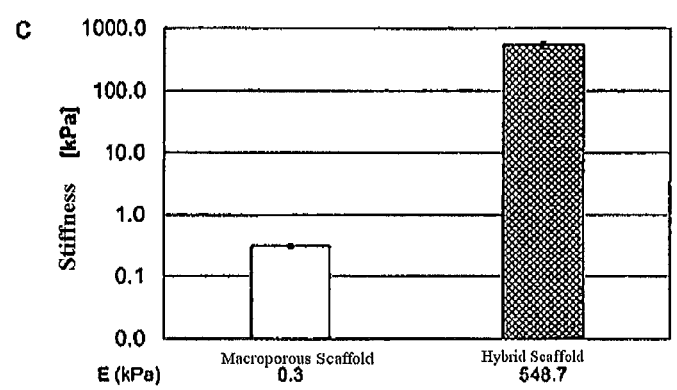
Figure 13:
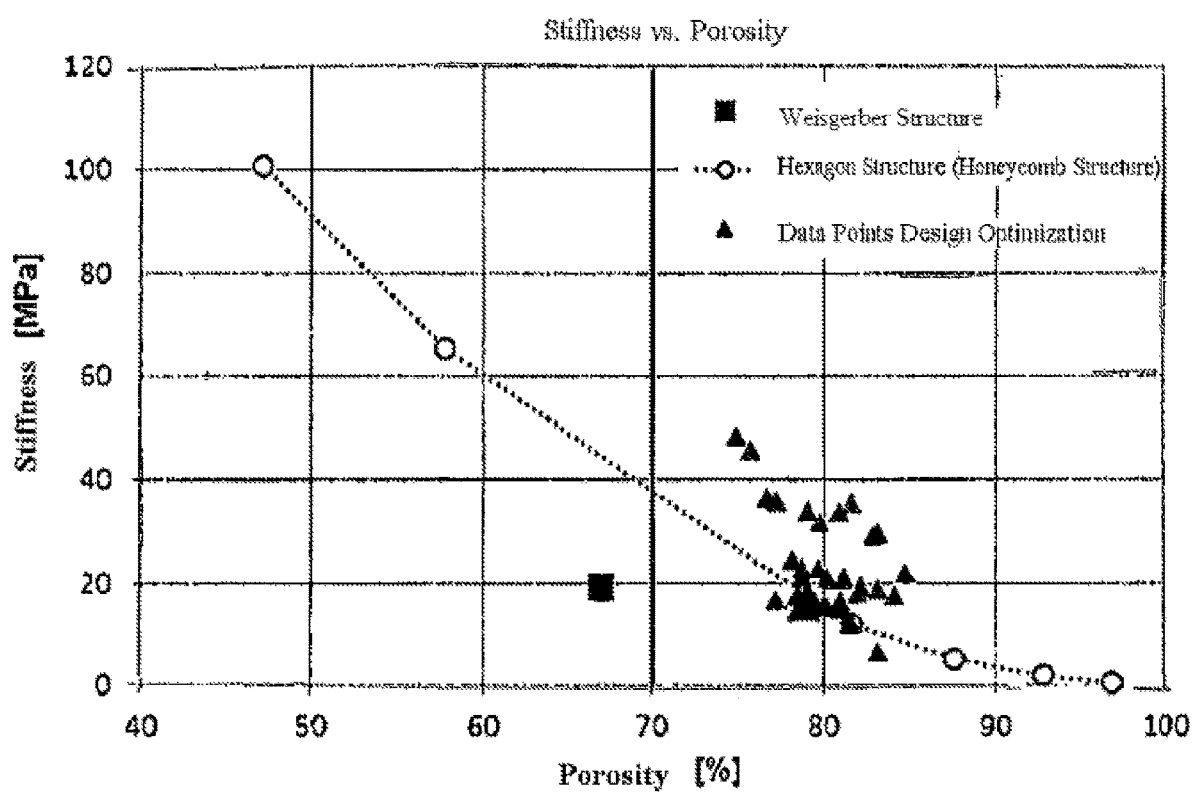

While the pure collagen scaffold collapses after wetting with aqueous solution (phosphate buffer) and thus alters its external shape (FIG. 12a), the mechano-hybrid scaffold shows no change in the outer geometry as a sign of the spanning function of the secondary structure (=skeleton!!) (FIG. 12b). FIG. 12 thus shows the mechanical stabilization of a collagen scaffold by introducing a 3D printed support structure made of PA to generate a mechano-hybrid scaffold. The images of FIG. 12 show the pure collagen scaffold (a) and the mechano-hybrid scaffold (b) after wetting with aqueous buffer solution. The result of the mechanical compression test shows the more than 1000-fold increase in scaffold stiffness by introducing the support structure (c). The elastic modulus of the pure collagen scaffold and the collagen/PA hybrid scaffold was determined by means of uniaxial mechanical compression testing in an open reservoir with aqueous solution ("unconfined compression test"). The elastic modulus E was analyzed in the linear region of the stress-strain curve. Mechanical testing revealed an increase in macroscopic stiffness from E=0.3 (±0.1) kPa (pure collagen scaffold) to 550 (±64) kP (mechano-hybrid scaffold), that is, more than 1000 fold (see FIG. 12c).

The invention claimed is:

1. A biomaterial comprising an openly porous, bioabsorbable first material fraction and a second material fraction that is stiffer than the first material fraction and forms a load-bearing support structure,
   wherein the second material fraction is an integral part of the biomaterial surrounded by the first material fraction, as in an endoskeleton, such that the first material fraction is structurally integrated into the second material fraction in a form-fitting manner,
   wherein the volume fraction of the stiffer material is less than 30% of a total volume of the biomaterial, the total volume comprising the volume of the biomaterial and the volume of voids enclosed by the biomaterial, and
   wherein the structural stiffness in MPa of the second material fraction is at least 10 times higher than the structural stiffness in MPa of the first material fraction as determined using the same methodology.

2. The biomaterial according to claim 1, wherein at least one material fraction is elastically deformable.

3. The biomaterial according to claim 1, wherein both material fractions are elastically deformable.

4. The biomaterial according to claim 1, wherein the volume fraction of the stiffer material is less than 25% of the total volume of the biomaterial.

5. The biomaterial according to claim 1, wherein the structural stiffness of the second material fraction is 100 times higher than that of the first material fraction.

6. The biomaterial according to claim 1, wherein an average elongation between 1% and 100% or compression between 1% and 30% is caused by tissue forces acting after implantation in the first material fraction.

7. The biomaterial according to claim 6 for cartilage regeneration, in which tissue forces acting on the biomaterial after implantation lead to a compression of the first material fraction between 4-12%.

8. The biomaterial according to claim 6 for bone regeneration, in which tissue forces acting on the biomaterial after implantation lead to a compression of the first material fraction between 0.04-4%.

9. The biomaterial according to claim 1, wherein the first material fraction serves as a support material for cell regeneration and as cell-controlling material and the second material fraction serves as a mechanically stabilizing element.

10. The biomaterial according to claim 1, wherein at least one material fraction has a structure configured to direct a regeneration process along a predetermined direction.

11. The biomaterial according to claim 1, wherein the first material fraction has a first region configured to direct a regeneration process along a first direction and the second material fraction has a second region configured to direct a regeneration process along a second direction different from the first direction.

12. The biomaterial according to claim 1, wherein at least one material fraction has a structure comprising repetitive units.

13. The biomaterial according to claim 1, wherein at least one material fraction contains components visible using X-ray, computer tomography, or magnetic resonance imaging methods.

14. The biomaterial according to claim 1, wherein at least one material fraction is deformable by an external stimulus for regeneration promotion.

15. The biomaterial according to claim 1, wherein the stiffness of the second material fraction is highest in the direction in which the largest forces act on the material after implantation in a tissue.

16. The biomaterial according to claim 1, wherein the second material fraction has an architecture configured to realize a predetermined macroscopic material stiffness.

17. The biomaterial according to claim 1, wherein the second material fraction comprises a plurality of structural elements selected from the group consisting of pore walls and webs, each structural element having a diameter differing from an average diameter of all the structural elements by less than a factor of two.

18. A method for producing the biomaterial according to claim 1, wherein the second material portion of an implant for the regeneration of a specific tissue is adjusted so that the elongations required for the regeneration of this tissue result in the first material fraction in the body and a collapse of the first material fraction is prevented.

19. The biomaterial according to claim 10, wherein the structure has an aspect ratio of at least threefold so that a largest distance and a smallest distance between structural elements of the structure along all spatial directions differs by at least threefold.

* * * * *